(12) United States Patent
Autera et al.

(10) Patent No.: US 11,099,108 B2
(45) Date of Patent: Aug. 24, 2021

(54) SYSTEMS AND METHOD FOR PROVIDING A GRAPHICAL USER INTERFACE FOR AUTOMATED DETERMINATION OF RANDOMIZED REPRESENTATIVE SAMPLING

(71) Applicant: QC LABS, Irvine, CA (US)

(72) Inventors: Tyler Autera, Irvine, CA (US); Brian Lannon, Long Beach, CA (US); Swetha Kaul, Huntington Beach, CA (US); Thomas Autera, Coto De Caza, CA (US)

( * ) Notice: Subject to any disclaimer, the term of this patent is extended or adjusted under 35 U.S.C. 154(b) by 461 days.

(21) Appl. No.: 16/198,466

(22) Filed: Nov. 21, 2018

(65) Prior Publication Data

US 2020/0158600 A1  May 21, 2020

(51) Int. Cl.
| | |
|---|---|
| *G01N 1/02* | (2006.01) |
| *G06Q 30/00* | (2012.01) |
| *G01N 33/00* | (2006.01) |
| *G06F 3/0484* | (2013.01) |
| *G06F 3/0481* | (2013.01) |

(52) U.S. Cl.
CPC ........... *G01N 1/02* (2013.01); *G01N 33/0098* (2013.01); *G06Q 30/018* (2013.01); *G06F 3/04815* (2013.01); *G06F 3/04845* (2013.01); *G06F 3/04847* (2013.01)

(58) Field of Classification Search
CPC ....................................................... G01N 1/02
USPC ......................................................... 702/32
See application file for complete search history.

(56) References Cited

U.S. PATENT DOCUMENTS

| | | | | |
|---|---|---|---|---|
| 5,890,150 | A * | 3/1999 | Ushijima | G06F 16/2462 707/714 |
| 6,278,989 | B1 * | 8/2001 | Chaudhuri | G06F 16/2462 |
| 9,542,776 | B2 * | 1/2017 | Clarberg | G06T 15/005 |
| 9,563,864 | B2 * | 2/2017 | Cantor | G06Q 10/063114 |
| 9,811,938 | B2 * | 11/2017 | Han | G06T 13/80 |
| 10,799,546 | B1 * | 10/2020 | Jansen | C07D 311/78 |
| 2004/0149021 | A1 * | 8/2004 | Kessler | G01N 29/38 73/105 |

(Continued)

OTHER PUBLICATIONS

"Matlab 7 Creating Graphical User Interface" by Mathworks, 480 pages, published on Mar. 2007 (Year: 2007).*

*Primary Examiner* — Reza Nabi

(57) ABSTRACT

A non-transitory storage medium having stored thereon logic is disclosed. The logic is executable by one or more processors to perform operations including: determining, according to first user input received via a user interface (UI), a type of sampling to be performed, and generating (i) a randomized sampling plan for a substance stored in a first container, and (ii) a corresponding data object representing a three-dimensional (3D) model of the first container, wherein the 3D model includes a plurality of increments, wherein a subset of the plurality of increments to be sampled includes a visual indicator. A first type of sampling to be performed includes bulk sampling, and a second type of sampling to be performed includes packaged sampling. The logic, when executed by the one or more processors, may perform further operations including receiving additional user input, via the UI, corresponding to information pertaining to sampling environment conditions.

20 Claims, 11 Drawing Sheets

(56) References Cited

U.S. PATENT DOCUMENTS

| | | | |
|---|---|---|---|
| 2005/0223337 A1* | 10/2005 | Wheeler | G06T 19/00 715/806 |
| 2007/0033120 A1* | 2/2007 | Sparaggis | G06Q 40/04 705/35 |
| 2008/0221849 A1* | 9/2008 | Angyal | G06F 30/20 703/14 |
| 2009/0055150 A1* | 2/2009 | Prior | G06F 19/00 703/11 |
| 2010/0026294 A1* | 2/2010 | Lustig | G01R 33/5616 324/307 |
| 2014/0184597 A1* | 7/2014 | Clarberg | G06T 17/20 345/423 |
| 2014/0267304 A1* | 9/2014 | Han | G06T 11/206 345/473 |
| 2014/0379610 A1* | 12/2014 | Lindeman | G01N 21/77 705/347 |
| 2015/0219610 A1* | 8/2015 | Jackson, Jr. | G01N 33/948 707/770 |
| 2016/0025753 A1* | 1/2016 | Khosropour | G01N 33/54306 506/9 |
| 2016/0093077 A1* | 3/2016 | Chardon | G06T 11/206 345/440 |
| 2017/0052106 A1* | 2/2017 | Hennig | G06K 9/00147 |
| 2017/0243352 A1* | 8/2017 | Kutliroff | G06T 19/006 |
| 2017/0333503 A1* | 11/2017 | Ayres | A61K 36/185 |
| 2019/0153345 A1* | 5/2019 | Lee | C10L 5/44 |
| 2019/0195852 A1* | 6/2019 | Bryant, Jr. | G01N 33/15 |
| 2019/0241322 A1* | 8/2019 | Blomberg | B65D 50/06 |
| 2019/0254325 A1* | 8/2019 | Munsell | A23L 2/52 |
| 2019/0383874 A1* | 12/2019 | Jaenisch | G06F 30/20 |
| 2020/0143563 A1* | 5/2020 | Liu | G06K 9/00805 |
| 2020/0156826 A1* | 5/2020 | Kilduff | B65D 85/52 |
| 2020/0158600 A1* | 5/2020 | Autera | G06F 3/0482 |
| 2020/0184312 A1* | 6/2020 | Lee | G06N 3/0436 |
| 2020/0302234 A1* | 9/2020 | Walters | G06K 9/628 |
| 2021/0046525 A1* | 2/2021 | Lee | B09B 3/0083 |

\* cited by examiner

*200* ⤹   *208*   *204*

| Sample | New Sampling Event / Company_1 / 50111 — *210* | | | ✕ |
|---|---|---|---|---|
| | Bulk Sampling *212* | | Packaged Sampling *214* | |
| 50217 | Mat_Y | BULK | 07/05/2018 14:35 | Smith_A | 0/10 |
| 50215 | Mat_Z | BULK | 07/05/2017 14:38 | Smith_A | 0/10 |
| 49957 | Mat_1 | BULK | 07/06/2018 13:53 | Smith_A | 9/10 |
| 50225 | Mat_2 | BULK | 07/11/2017 10:12 | Smith_B | 0/34 |
| 50220 | Mat_3 | BULK | 07/11/2017 10:19 | Smith_C | 0/34 |

*202* brackets the data rows.

New Sampling Event / Company_1 / 50111 — *210*

Batch Size in Lbs
Maximum 50 lbs

Number Containers

——— Container Info ———

Container Type
Rectangular

Length

Width

Height

Dead Space Height

ADVANCED OPTIONS

[ Generate Sampling Model ] — *216*

New Sampling Event / Company_1 / 50111 —— *210*

Total Units
[ ]

Number of Pallets
[ ]

Unit Info

Weight of Substance in unit
[ Usually .5 or 1 (in grams) ]

Unit Length (inches)
[ ]

Unit Width (inches)
[ ]

Unit Height (inches)
[ ]

Pallet Info

Of Units Long
[ ]

Of Units Wide
[ ]

Of Units High
[ ]

[ Generate Sampling Model ] — *216*

*FIG. 2E*

SYSTEMS AND METHOD FOR PROVIDING A GRAPHICAL USER INTERFACE FOR AUTOMATED DETERMINATION OF RANDOMIZED REPRESENTATIVE SAMPLING

FIELD

Embodiments of the disclosure relate to the field of substance sampling. More specifically, embodiments of the disclosure relate to a system for automated sample plan generation for various substances, e.g., plant substances, in order to ensure compliance with one or more predefined laws, regulations or requirements.

GENERAL BACKGROUND

In 1996, California became the first state to legalize medical *cannabis* with the passage of the Compassionate Use Act of 1996 (Proposition 215). Subsequently, in November of 2016, the Adult Use of Marijuana Act (Proposition 64) was approved by California voters, which legalized the recreational use of *cannabis* within the state. Prior to reaching patients or consumers in California, *cannabis* samples are required to undergo laboratory testing, e.g., "sampling." Regulatory agencies including the Bureau of *Cannabis* Control (BCC), Department of Food and Agriculture, Department of Public Health and *Cannabis* Regulatory Authority (CRA) oversee the rules and regulations for such laboratory testing.

As one example, the BCC regulates the testing of various forms of *cannabis* according to Title 16 of the California Code of Regulations, Section 5715, among others. Specifically, the BCC has rolled out a phase-in requirement for testing including a first phase beginning Jan. 1, 2018, a second phase beginning Jul. 1, 2018 and a third phase beginning Dec. 31, 2018. The various phases require testing of samples of differing *cannabis* forms and products as well as testing for various substances within the *cannabis* forms and products. For example, the first phase rolled out Jan. 1, 2018 required that inhalable *cannabis*, inhalable *cannabis* products and other *cannabis* and *cannabis* products be tested for cannabinoids, category I residual pesticides and microbial impurities (e.g., *Escherichia coli* and *Salmonella* spp.) while only inhalable *cannabis* was required to be tested by moisture content. Each phase rolled out several new requirements that make *cannabis* sample laboratory testing a complex field.

As each phase rolls out, a surprising percentage of samples fail the new requirements. For example, approximately 20 percent of the samples tested in California following the second phase of July 1 failed the new safety requirements. Therefore, it is imperative that the laboratory testing be precise and comprehensive in order to provide patients and consumers with a safe and accurately labeled *cannabis* product. Thus, a standardized method and procedure for obtaining samples would greatly improve the accuracy, comprehensiveness and efficiency of laboratory sampling.

As the name implies, sampling is the selection of a subset within a batch of a substance on which testing is performed in order to estimate characteristics of the whole. Performing sampling of a plant species is often times difficult as chemical properties of the plant species vary between plants within a plant species, and even from flower to flower within a single plant. In addition, sampling a flower, or flower bud. of a plant, e.g., *cannabis* flower bud, should be performed in such a manner as to avoid damaging the flower bud, assuming the flower bud will be sold after sampling. Therefore, the variation in chemical properties from plant to plant, and even flower bud to flower bud, places a burden on the sampling agency to ensure that the subset selected for sampling is actually representative of the whole of the batch.

In particular, when a third-party sampling agency performs the sampling (often required by applicable laws, rules, regulations, contracts, etc., for certain plant produces, e.g., *cannabis*), it is integral that the sampling being randomized and that growers are not able to knowingly provide the sampling agency with unrepresentative samples. To complicate matters for sampling agencies, there is no industry standard bin or container. Therefore, it is commonplace to have batches provided to sampling agencies in various containers (e.g., that differ in dimensions, sizes, shapes, etc.). As a result, each batch sampled by a sampling agency may require the generation of a new sampling plan with the sampling agency being tasked with ensuring the subset sampled is representative of the whole and also conforms to any applicable laws, rules, regulations, contracts, etc. Additionally, performance of a sampling process on a batch stored in a large container is often complicated by the fact that the technician performing the sampling often must determine how to select a random sample representative of the batch on the fly while attempting to take into account all applicable laws, rules, regulations, contracts, etc.

BRIEF DESCRIPTION OF THE DRAWINGS

Embodiments of the invention are illustrated by way of example and not by way of limitation in the figures of the accompanying drawings, in which like references indicate similar elements and in which:

FIG. 2C is an exemplary embodiment of the interactive user interface of FIGS. 2A-2B configured to receive user input corresponding to the automatic generation of the sampling plan and the 3D model of the sampling plan by the automated representative sampling plan generation system of FIG. 6 in accordance with some embodiments;

FIG. 2D is an exemplary embodiment of the interactive user interface of FIGS. 2A-2C configured to receive user input corresponding to the automatic generation of the sampling plan and the 3D model of the sampling plan by the automated representative sampling plan generation system of FIG. 6 in accordance with some embodiments;

FIG. 2E is an exemplary embodiment of the interactive user interface of FIGS. 2A-2D configured to receive user input corresponding to the automatic generation of the sampling plan and the 3D model of the sampling plan by the automated representative sampling plan generation system of FIG. 6 in accordance with some embodiments;

DETAILED DESCRIPTION

Figure 1A:
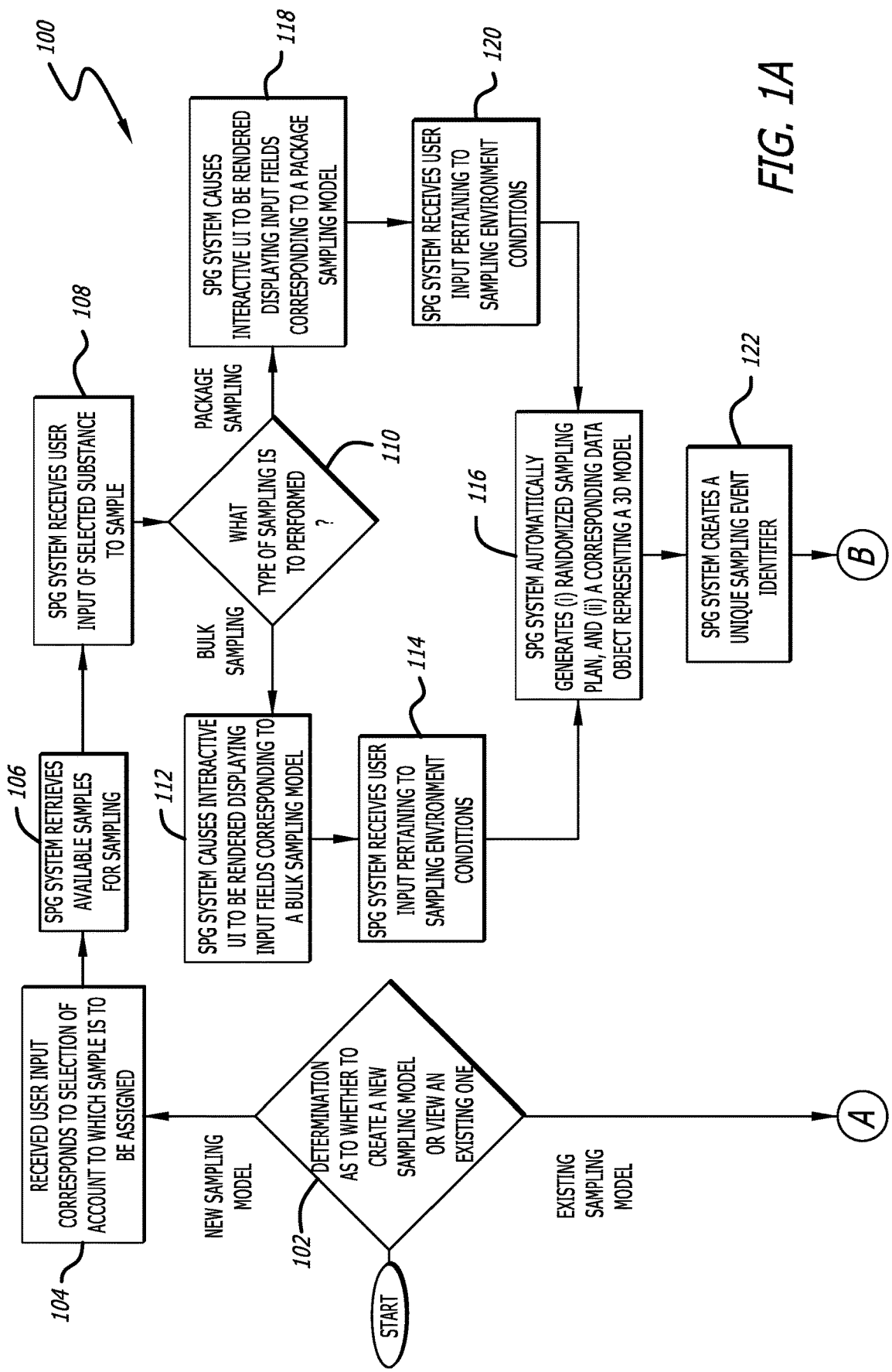
FIGS. 1A-1B illustrate a flowchart of an exemplary method for automatically generating three-dimensional (3D) model of a randomized sampling plan using an automated representative sampling plan generation system in accordance with some embodiments.

Various embodiments of the disclosure relate to an automated, computerized method for generating a random sampling plan of a substance, such as gravel, solid chemical substances and plant particles for example. In particular, the automated, computerized method may generate a three-dimensional (3D) graphic representation of a container (or package) in which a substance to be sampled is stored based on received user input. In addition, during generation of the randomized sampling plan and the 3D graphic representation, the computerized method divides the container into increments (e.g., segments or portions) and provides a visual indication as to which increments are to be sampled. Thus, the computerized method receives user input pertaining to a container storing a substance to be sampled and generates a randomized sampling plan, which includes generation of a 3D representation of the container divided into increments and further provides a visual indication as to which increments are to be sampled.

As will be discussed in further detail below and in combination with the figures, the computerized method causes the rendering of an interactive user interface (UI) that displays the 3D graphic representation of the container. The interactive UI may also include a plurality of text boxes corresponding to the increments to be sampled. For example, each text box may correspond to a single increment to be sampled (with appropriate and corresponding labeling appearing on the 3D graphic representation) and include a recommended sampling amount for each increment. After obtaining a sample from a particular increment, the user (i.e., sampler) provides user input to the text box with an actual sampling amount (e.g., 20 grams may be recommended but an actual sampling amount may be 22 grams). When an actual sampling amount varies from the recommended amount, the computerized method may automatically recalculate recommended sampling amounts for the remaining increments. The recalculation may include (1) recalculation of a recommended sampling amount for each of the remaining increments to be sampled, and/or (2) recalculation of which increments are to be sampled (causing the 3D graphic representation to be updated as a result).

I. Terminology

In the following description, certain terminology is used to describe features of the invention. For example, in certain situations, the term "logic" may be representative of hardware, firmware and/or software that is configured to perform one or more functions. As hardware, logic may include circuitry having data processing or storage functionality. Examples of such circuitry may include, but are not limited or restricted to a microprocessor, one or more processor cores, a programmable gate array, a microcontroller, a controller, an application specific integrated circuit, wireless receiver, transmitter and/or transceiver circuitry, semiconductor memory, or combinatorial logic.

Logic may be software in the form of one or more software modules, such as executable code in the form of an executable application, an application programming interface (API), a subroutine, a function, a procedure, an applet, a servlet, a routine, source code, object code, a shared library/dynamic link library, or one or more instructions. These software modules may be stored in any type of a suitable non-transitory (computer-readable) storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the executable code is stored in persistent storage.

The term "processing" may include execution of a binary or launching an application wherein launching should be interpreted as placing the application in an open state and, in some implementations, performing simulations of actions typical of human interactions with the application. For example, the application, an Internet browsing application, may be processed such that the application is opened and actions such as visiting a website, scrolling the website page, and activating a link from the website are performed (e.g., the performance of simulated human interactions).

The term "object" generally refers to a collection of data, whether in transit (e.g., over a network) or at rest (e.g., stored), often having a logical structure or organization that enables it to be categorized or typed for purposes of analysis. During analysis, for example, the object may exhibit a set of expected and/or unexpected characteristics and, during processing, a set of expected and/or unexpected behaviors, which may evidence the presence of malware and potentially allow the object to be categorized or typed as malware. In one embodiment, an object may include a binary file that may be executed within a virtual machine. Herein, the terms "binary file" and "binary" will be used interchangeably.

The term "network device" may be construed as any intelligent electronic device with the capability of connecting to a network. Such a network may be a public network such as the Internet or a private network such as a wireless data telecommunication network, wide area network, a type of local area network (LAN), or a combination of networks.

Examples of a network device may include, but are not limited or restricted to, a laptop, a mobile phone, a tablet, etc.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

The invention may be utilized for automatically developing a randomized sampling plan and generating a display screen illustrating the randomized sampling plan. As this invention is susceptible to embodiments of many different forms, it is intended that the present disclosure is to be considered as an example of the principles of the invention and not intended to limit the invention to the specific embodiments shown and described.

Figure 1B:
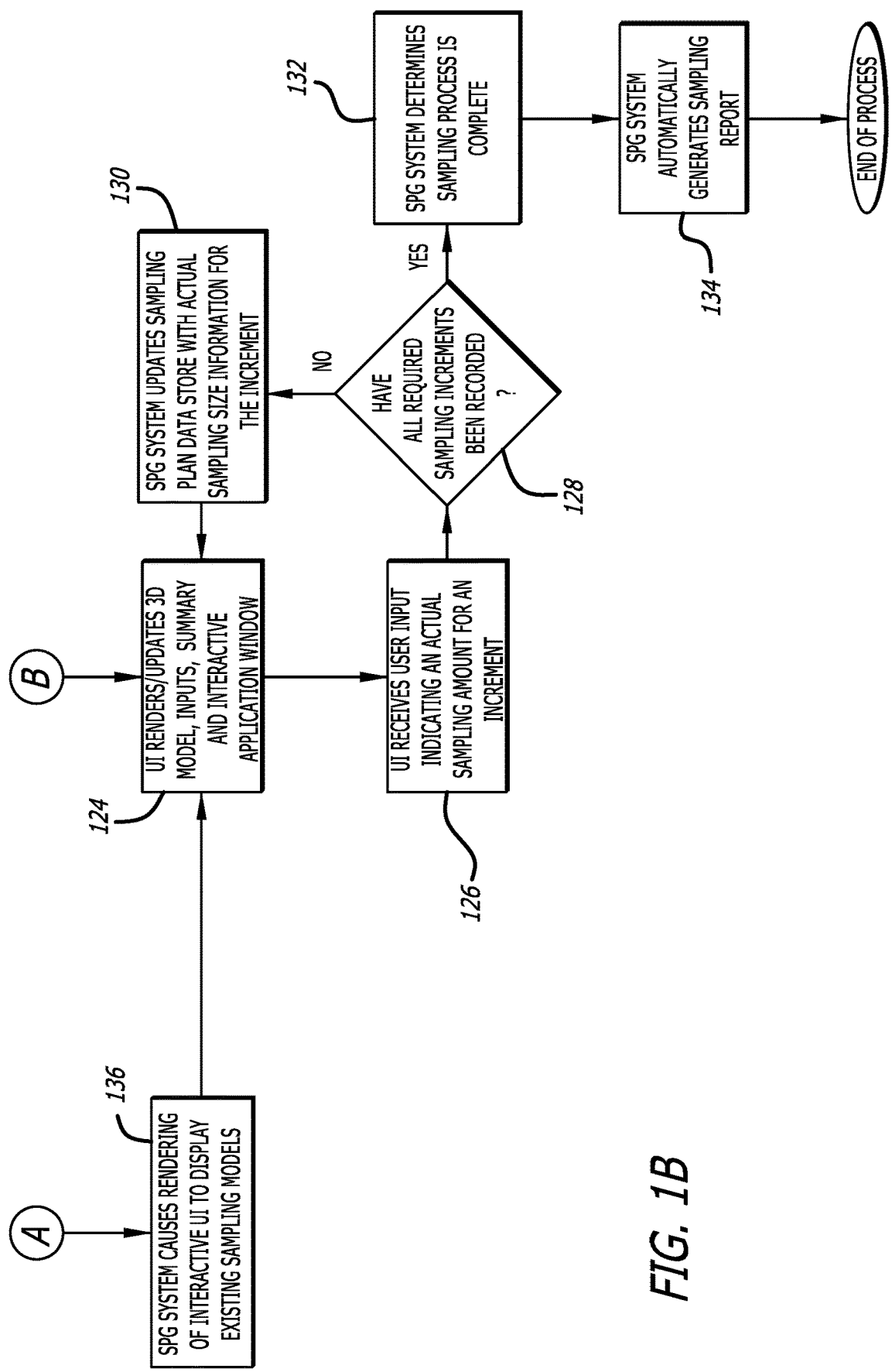

II. Automated Generation of a 3D Model of a Randomized Sampling Plan Methodology Referring to FIGS. 1A-1B, a flowchart illustrating an exemplary method for automatically generating a randomized sampling plan and a corresponding three-dimensional (3D) model using an automated representative sampling plan generation system is shown in accordance with some embodiments. Each block illustrated in FIGS. 1A-1B represents an operation performed in the method 100 of automatically generating a randomized sampling plan. Additionally, the FIGS. 2A-5B corresponds to one example implementation of the method 100. Various exemplary user interfaces discussed in the description of method 100 are illustrated in the FIGS. 2A-5B.

Figure 6:
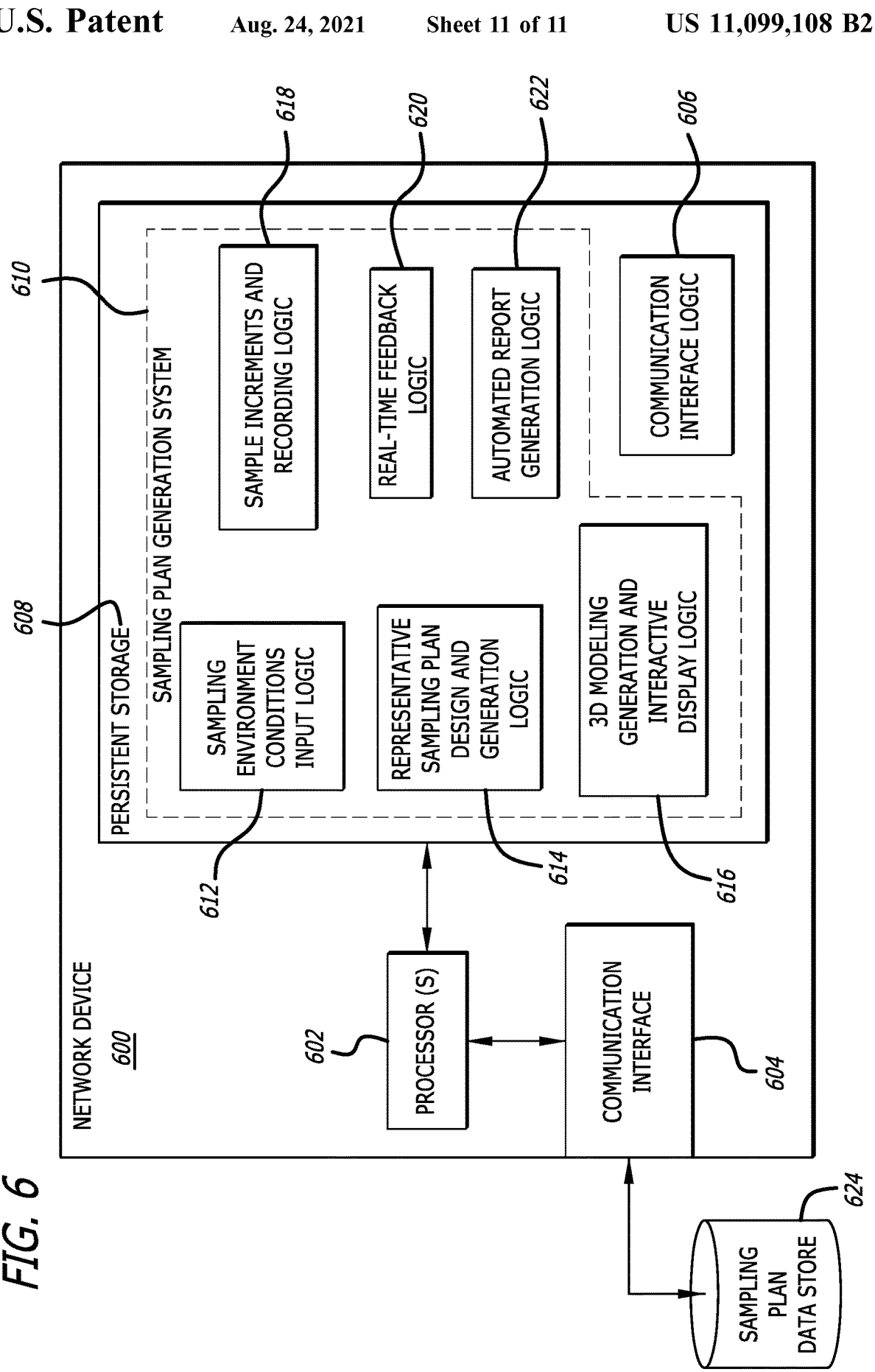
FIG. 6 is an exemplary embodiment of a logical representation of the automated representative sampling plan generation system in accordance with some embodiments.

Referring now to FIG. 1A, the automated representative sampling plan generation (SPG) system 610, as seen in FIG. 6, receives user input corresponding to a decision to create a new randomized sampling plan or view an existing sampling plan (block 102).

Upon receiving user input corresponding to a decision to create a new randomized sampling plan, further user input is received corresponding to the selection of an account to whom the sampling plan is to be assigned (block 104). Subsequent to receiving the selection of an account, the SPG system 610 retrieves information pertaining to the substance to be sampled (block 106). In one embodiment, the SPG system 610 may retrieve the substance information via an application programming interface (API). Upon retrieving the substance information, the SPG system 610 causes an interactive user interface (UI) to be rendered that is configured to (i) display the retrieved substance information, and (ii) receive user input corresponding to a selection of additional substance and sampling information (block 108).

Based on the selection of a substance to be sampled, the SPG system 610 receives further user input via an interactive UI that indicates a selection of a type of sampling to be performed (block 110). When the user input indicates that bulk sampling is to be performed, the SPG system 610 causes an interactive UI to be rendered that displays a plurality of input fields corresponding to information to be used in the automated generation of a randomized bulk sampling plan (block 112). The term "bulk sampling" refers to performing a sampling process on content that is stored or presented in a bulk container. One example of a bulk container may include a pallet pack container having dimensions of 45"×40"×48" (height×width×length), having an internal volume of 36 cubic ft. (ft$^3$) and a weight capacity of 2000 lbs. However, such is merely only one example and inclusion of such is in no way intended to limit the definition of "bulk container."

The interactive UI referenced above with respect to block 112 includes a plurality of input fields corresponding to information to be used in the automated generation of a randomized bulk sampling plan. An exemplary interactive UI may be seen in at least FIGS. 2D-2E. In particular, the interactive UI seeks to obtain, through the input fields, information pertaining to sampling environment conditions. Examples of sampling environment conditions for bulk sampling may include, but are not limited or restricted to, container size, amount of product in the batch, minimum of percentage of the batch to be sampled, total weight or units of the batch, minimum sample increment dimensions, etc. It should be noted, that some of the sampling environment conditions may be automatically determined by the SPG system 610 as a result of laws, rules, regulations, ordinances, contracts, etc.

At block 114, the SPG system 610 receives user input pertaining to the sampling environment conditions via the plurality of fields displayed in the interactive UI. At block 116, the SPG system 610 automatically generates (i) a randomized sampling plan based on the sampling environment conditions, and (ii) a corresponding data object representing a 3D model. The 3D model may represent either a container or a package in which the substance is stored. Further, a randomized sampling plan may encompass multiple containers or packages, and in such a case a data object representing a 3D model would be generated for each container or package. Specifically, the generation of the data object representing a 3D model includes the transformation (or translation) of mere descriptive information of a container or package (e.g., dimensions) into a data object that provides instructions for rendering a 3D model of the container or package. Further, the generation of the data object includes analysis of the descriptive information of the container or package as well as received sampling environment conditions in order to breakdown the container or package dimensions into a plurality of increments. Even further, the randomized sampling plan is then analyzed to determine a subset of the plurality of increments that are to be analyzed and associate each increment of the subset with a visual indicator that is to be displayed when the 3D model is rendered.

Referring again to block 110, based on the selection of a substance to be sampled, the SPG system 610 receives further user input via an interactive UI that indicates a selection of a type of sampling to be performed. When the user input indicates that package sampling is to be performed, the SPG system 610 causes an interactive UI to be rendered that displays a plurality of input fields corresponding to information to be used in the automated generation of a package sampling plan (block 120). The term "package sampling" refers to sampling of a substance that arrives at the sampling agency (or is provided to a sampling technician) in a sealed package (e.g., an airtight vacuum packaging bag). Examples of sampling environment conditions for package sampling may include, but are not limited or restricted to, package size, amount of product in a package, number of packages in a batch, minimum of percentage of the batch to be sampled, total weight or units of the batch, minimum sample block dimensions, etc.

Figure 3A:
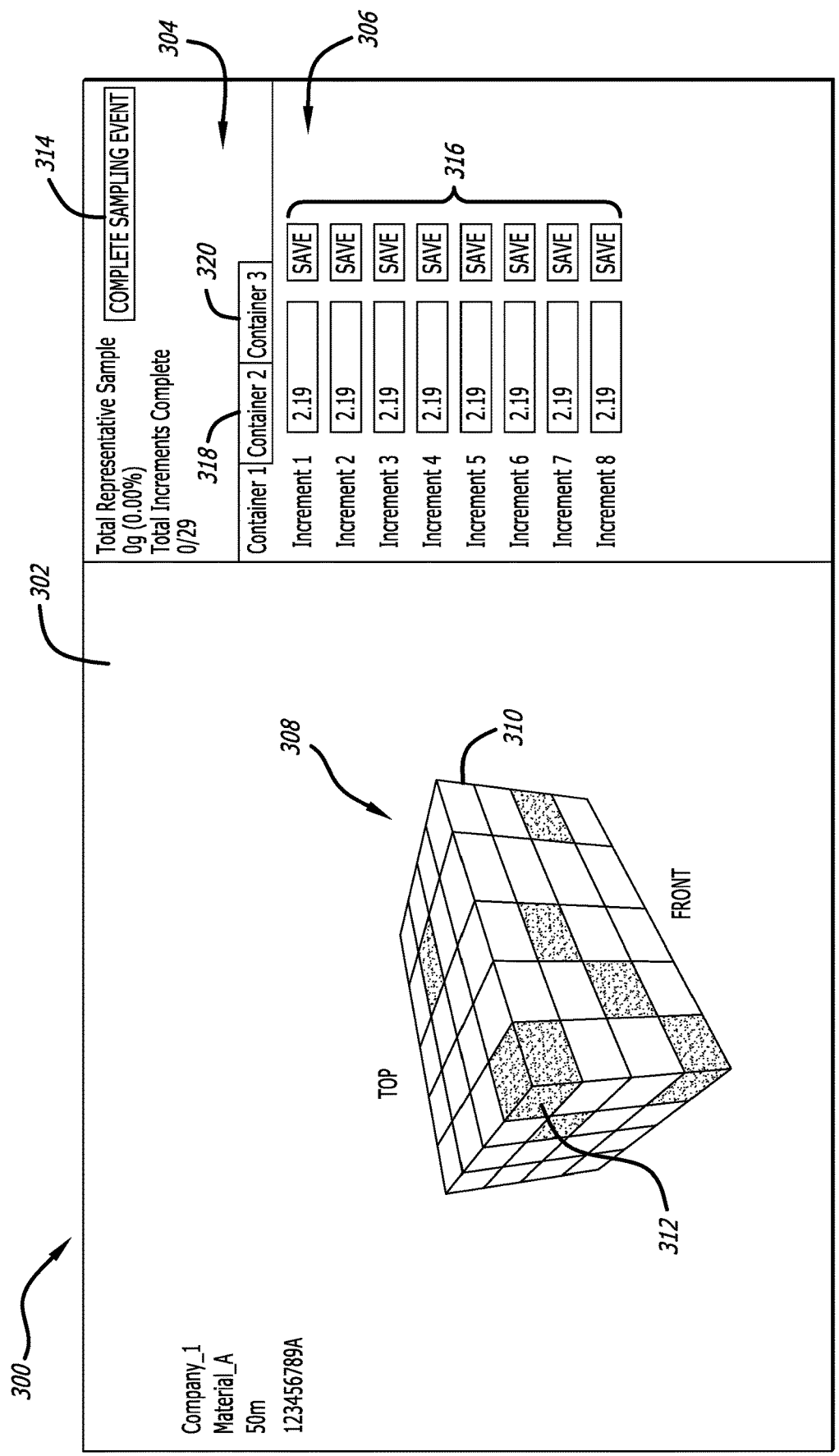
FIG. 3A is an exemplary embodiment of an interactive user interface illustrating a rendered 3D model of the sampling plan by the automated representative sampling plan generation system of FIG. 6 in accordance with some embodiments.
Figure 3B:
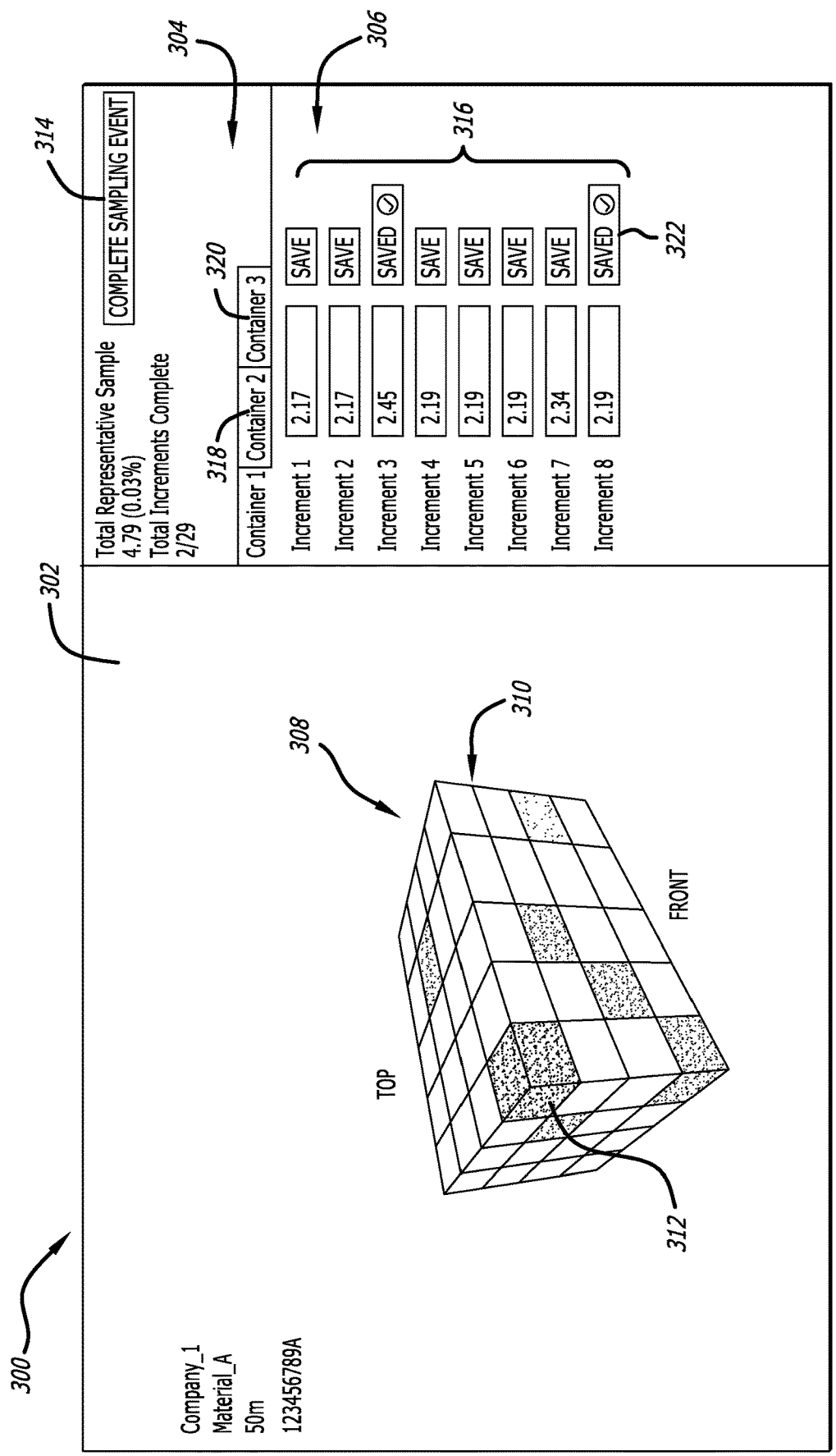
FIG. 3B is an exemplary embodiment of the interactive user interface illustrating the rendered updated 3D model of the sampling plan from FIG. 3A in accordance with some embodiments.

Following the generation of the randomized sampling plan and data object representing a 3D model, the SPG system 610 creates a unique sampling event identifier for purposes of storing the sampling plan and data object, for example within the sampling plan data store 624 (block 122). Continuing on to FIG. 1B, the SPG system 610 causes the rendering of a display screen illustrating the 3D model representing the randomized sampling plan, for example, as seen in FIGS. 3A-3B (block 124). The display screen may include information pertaining to a number of increments per container as well as a recommended sampling size (e.g., weight) for each increment on a per container basis (or per package). In addition, the interactive UI may include a plurality of user input fields (e.g., text boxes, drop-down menus, buttons, radio dials, check boxes, etc.) that are configured to receive input indicating an actual sampling size for each increment. The interactive UI illustrating the 3D model and the corresponding information will be discussed in depth below with respect to FIGS. 3A-3B.

At block 126, the interactive UI receives user input indicating the actual sampling size for an increment. In response to receiving user input indicating the actual sampling size for an increment, the SPG system 610 then makes a determination as to whether a sampling size has been received for all required increments (block 128). When not all required actual sampling sizes have been received, the SPG system 610 updates the sampling plan data store 624 with the actual sampling size for the increment as received with respect to block 126 (block 130).

Following the updating of the sampling plan data store 624, the SPG system 610 returns to block 124 and causes the rendering of an updated interactive UI which includes display of all received actual sampling sizes as well as the recommended sampling sizes for all remaining increments for which an actual sampling size has not been received. It should be noted that the SPG system 610 may also update the recommended sampling size for each remaining increment based on user input of actual sampling sizes. In such an embodiment, the SPG system 610 may analyze the any rules, regulations, contracts, etc., and the previously generated sampling plan in light of received data pertaining to actual sampling values. The SPG system 610 may determine (i) whether each of the actual sampling values received conform to the applicable laws, rules, regulations, contracts, etc., (ii) determine how much actual sampling information has yet to be received, and, if needed, (iii) recalculate one or more recommended sampling values for the remaining sampling information that is yet to be received (i.e., when actual sampling values are greater than or less than the recommended values but still conform to the applicable laws, rules, regulations, contracts, etc., the remaining recommended values may need to be adjusted to ensure that the overall sampling procedure will still conform). In some embodiments, the recalculation may involve the regeneration of the data object representing the 3D model of the container that indicates which increments are to be sampled. For example, when one or more actual sampling values are greater than or less than the recommended sampling values in a particular area of a container, the increments to be sampled may need to be altered in order to conform to randomization requirements set forth in the applicable laws, rules, regulations, contracts, etc.

Referring again to block 128, when all required actual sampling sizes have been received, the SPG system 610 determines the randomized sampling process has been completed (block 132). In one embodiment, the determination that the randomized sampling process has been completed is made in response to receipt of user input activating a button indicating the sampling process has been completed. In another embodiment, the SPG system 610 may automatically determine the sampling process is complete based on entry of the sampling size for each required increment.

Following a determination that the sampling process is complete, the SPG system 610 automatically generates a report that summarizes the sampling process and gives detailed information indicating that the sampling process complied with all applicable laws, rules, regulations, contracts, etc. (block 134).

Referring again to block 102 and upon receiving user input corresponding to a decision to view an existing randomized sampling plan, the SPG system 610 causes rendering of an interactive UI configured to display existing sampling plans for selection by a user (block 136). Upon selection of an existing sampling plan, the SPG system 610 causes the rendering of a display screen illustrating the 3D model representing the randomized sampling plan (block 124) and the method 100 continues therefrom as discussed above.

III. Interactive User Interface Implementation

Figure 2A:
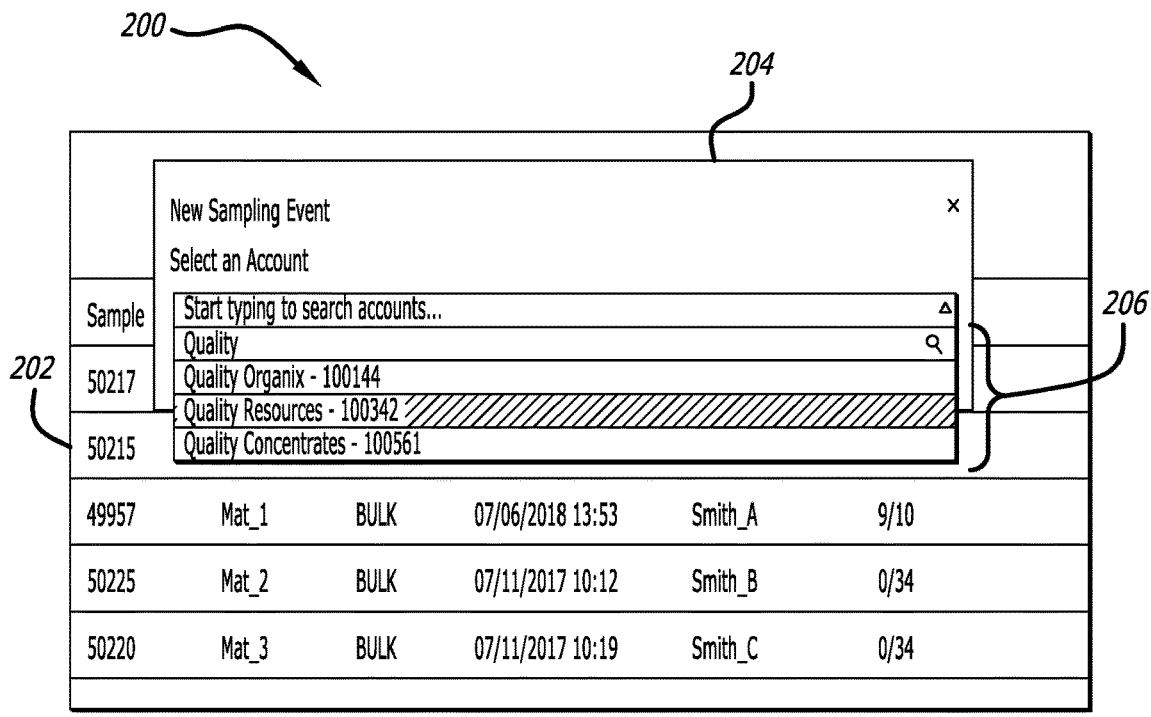
FIG. 2A is an exemplary embodiment of a first interactive user interface configured to receive user input corresponding to the automatic generation of a sampling plan and a 3D model of the sampling plan by the automated representative sampling plan generation system of FIG. 6 in accordance with some embodiments.

Referring now to FIG. 2A, an exemplary embodiment of a first interactive user interface configured to receive user input corresponding to the automatic generation a sampling plan and a 3D model of the sampling plan by the automated representative sampling plan generation system of FIG. 6 is shown in accordance with some embodiments. The interactive user interface 200 includes a display screen 202 (e.g., a background screen) and a pop-up 204. Shown in this embodiment, the display screen 202 may list a history of sampling procedures.

The pop-up 204 enables a user to provide user input corresponding to a selection of an account to which a new sampling plan is to be assigned (corresponding to block 104 of FIG. 1A). The pop-up 204 illustrates a drop-menu displaying a plurality of accounts 206. It should be noted that pop-up 204 may utilize alternative user input methodologies to enable a user to provide user input and such alternative user input methodologies are within the scope of the invention. The plurality of accounts 206 may be stored in the sampling plan data store 624 as seen in FIG. 6. In some embodiments, although now shown, the sampling plan data store 624 may be included in the SPG system 610 and stored locally on a network device on which the SPG system 610 is stored and being executed.

Figure 2B:
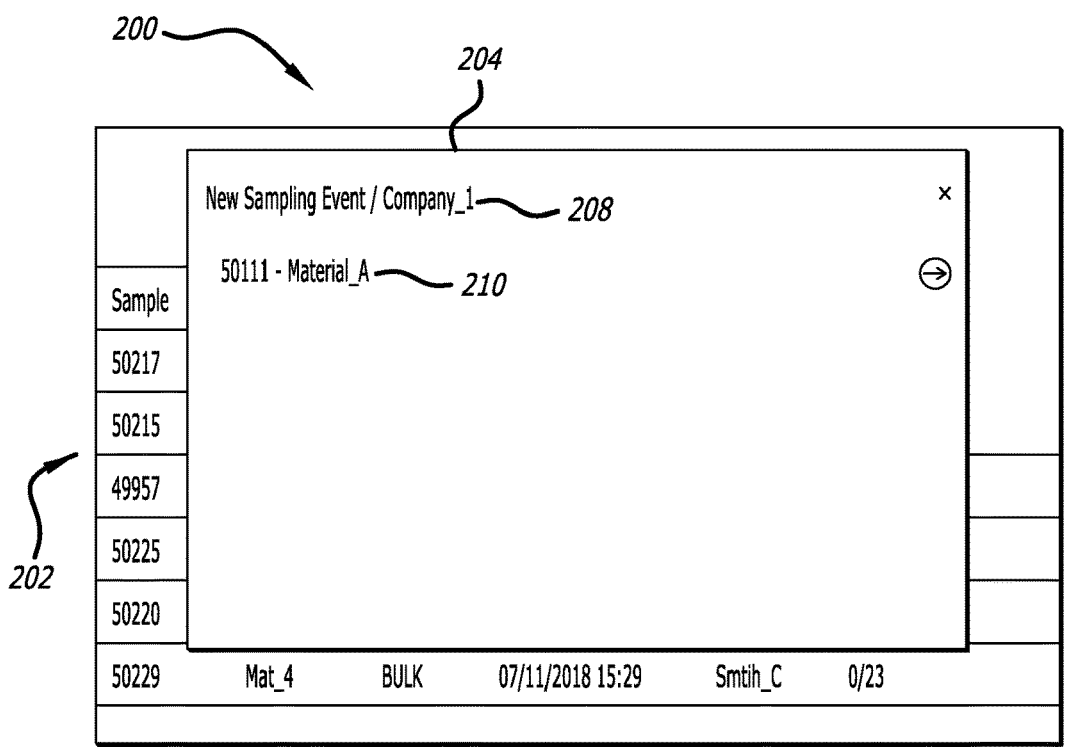
FIG. 2B is an exemplary embodiment of the interactive user interface of FIG. 2A configured to receive user input corresponding to the automatic generation of a sampling plan and the 3D model of the sampling plan by the automated representative sampling plan generation system of FIG. 6 in accordance with some embodiments.

Referring now to FIG. 2B, an exemplary embodiment of the interactive user interface of FIG. 2A configured to receive user input corresponding to the automatic generation of the sampling plan and the 3D model of the sampling plan is shown in accordance with some embodiments. FIG. 2B illustrates the interactive user interface 200 with the display screen 202 and an updated pop-up 204. The pop-up 204 of FIG. 2B has been updated to display that user input has been received indicating that the new sampling plan is to be assigned to Company_1, wherein the listing 208 indicates a status: a new sampling event has been selected and the new sampling plan is to be assigned to Company_1 (corresponding to block 108 in FIG. 1A). Additionally, the updated pop-up 204 illustrates information stored in the sampling plan data store 624 corresponding to the Company_1 includes "50111—Material A" (210), which may represent an identifier for a material previously sampled for Company_1. In some embodiments, multiple materials may be listed based on previous samplings performed for a selected account. In addition, some embodiments may include an additional user input methodology that enables a user to provide user input that adds a new material to the selected account.

Referring now to FIG. 2C, an exemplary embodiment of the interactive user interface of FIGS. 2A-2B configured to receive user input corresponding to the automatic generation of the sampling plan and the 3D model of the sampling plan is shown in accordance with some embodiments. FIG. 2C illustrates the display screen 202, which is seen in more detailed compared to FIG. 2B as displaying a listing of past sampling procedures. Additionally, the pop-up 204 has been updated based on user input received previously as discussed with respect to FIG. 2B to display the listing 208 indicating an updated status that includes a new sampling event has been selected and the new sampling plan is to be assigned to Company_1 and sampling of material "50111" (210). Furthermore, the updated pop-up 204 includes two buttons 212 and 214 (user input methodologies) providing the user the ability to select a sampling type: bulk sampling 212 or packaged sampling 214 (corresponding to block 110 in FIG. 1A).

Referring now to FIG. 2D, an exemplary embodiment of the interactive user interface of FIGS. 2A-2C configured to receive user input corresponding to the automatic generation of the sampling plan and the 3D model of the sampling plan is shown in accordance with some embodiments. FIG. 2D illustrates another update to pop-up 204 (now almost fully covering the display screen 202) based on received user input that indicates the sampling is to be bulk sampling (i.e., selection of button 212 in FIG. 2C). The updated pop-up 204 has been rendered to display a plurality of text fields (also referred to herein as text boxes or input fields) that are configured to receive user input pertaining to bulk sampling (corresponding to box 112 of FIG. 1A). Examples of information that the text fields may be configured to receive include, but are not limited or restricted to, batch size (e.g., in pounds), number of containers, container type (e.g., shape), container dimensions (length, width, height), etc. The information received may correspond to sampling environment conditions (corresponding to block 114 of FIG. 1A). In some embodiments, user input may be required in one or more of the text fields prior to the SPG system 610 generating a randomized sampling plan. FIG. 2D also illustrates that the pop-up 204 may include a button 216 configured to receive user input (e.g., activation of the button 216) and responsive thereto, initiate the automated generation of a randomized sampling plan.

Referring now to FIG. 2E, an exemplary embodiment of the interactive user interface of FIGS. 2A-2C configured to receive user input corresponding to the automatic generation of the sampling plan and the 3D model of the sampling plan is shown in accordance with some embodiments. FIG. 2E illustrates yet another update to pop-up 204 based on received user input that indicates the sampling is to be packaged sampling (i.e., selection of button 214 in FIG. 2C). The updated pop-up 204 has been rendered to display a plurality of text fields that are configured to receive user input pertaining to package sampling (corresponding to boxes 118 of FIG. 1A). Examples of information that the text fields may be configured to receive include, but are not limited or restricted to, total units, number of pallets (e.g., the term "pallet" may refer to a container or method of transporting a plurality of units), weight of content per unit, unit dimensions (length, width, height), etc. The information received may correspond to sampling environment conditions (corresponding to block 120 of FIG. 1A). In some embodiments, user input may be required in one or more of the text fields prior to the SPG system 610 generating a randomized sampling plan. FIG. 2E also illustrates that the pop-up 204 may include the button 216 as seen in FIG. 2D.

Referring to FIG. 3A, an exemplary embodiment of an interactive user interface illustrating a rendered 3D model of the sampling plan by the automated representative sampling plan generation system of FIG. 6 is shown in accordance with some embodiments. FIG. 3A illustrates an interactive UI 300 that has been rendered (e.g., on a display screen of an electronic device such as a tablet, mobile phone or desktop computer). The interactive UI 300 includes display sections 302, 304 and 306. The display section 302 illustrates a 3D graphical representation ("3D model") 308 of the automatically generated randomized sampling plan. Herein term "sampling plan" may generally refer to a recommendation for sampling a portion of a substance stored within a container. Further, a sampling plan may include a breakdown of the container into a plurality of increments, where a subset of the plurality of increments are indicated for sampling. In some embodiments, a sampling plan may include a listing of the subset of increments with a recommended sampling amount and some embodiments of a sampling plan may include a 3D model of the container wherein the subset of increments to be sampled are highlighted (e.g., emphasized over others). The 3D model 308 includes a graphical representation of the container storing the substance to be sampled divided into a plurality of increments 310. Specifically, the 3D model 308 visually distinguishes the increments to be sampled from those that are not included in the sampling. As one example illustrated in FIG. 3A, the increment 312 is shaded as compared to other increments that are not included in the sampling. The shading illustrated in FIG. 3A is merely one example of a visual indicator and other visual indications have been contemplated and are within the scope of the invention (e.g., striped, alternative colors, numbering, dotted, etc.). In some embodiments, the interactive UI 300 may receive user input causing the 3D model 308 to be rotated according to one or more axes. This provides an advantage to the user, sampler, technician, etc., of being able to determine exactly which increment is to be sampled.

The display section 304, i.e., a sampling status display section, provides information pertaining to the status of the sampling. The information displayed in the sampling status display section 304 may include the percentage of the sampling process that is complete, a total sampled weight, a total number of increments sampled, a ratio of sampled increments-to-increments to be sampled, etc.

The sampling status display section 304 may also include a button 314 that is configured to receive user input indicating that the sampling process is complete. In response to receiving user input activating the button 314, the SPG system 610 may initiate a verification process that verifies all required user input has been received. For example, the required user input may include text entered into each text field corresponding to an increment to be sampled (i.e., the listing of text boxes 316). Further, the verification process may verify that the text entered is in a required format, such as a decimal number. In yet some embodiments, the verification process may compare the decimal number entered into each text box 316 to ensure that the entered decimal number is within a specified range (e.g., plus or minus a specified amount from the recommended sampling value). By performing a verification process prior to completing the sampling procedure, the SPG system 610 automatically verifies that the sampling will conform to all necessary requirements (e.g., applicable laws, rules, regulations, mandates from inspection/licensing authorities or agencies, etc.). As is discussed throughout, the user input methodologies illustrated in FIGS. 3A-3B are merely examples and the disclosure is not intended to be limited thereto. Alternative user input methodologies have been contemplated, e.g., radio dials, drop-down menus, etc., and should be considered within the scope of the disclosure although now shown in the each figures discussed herein.

The display section 306 includes a listing of increments 316 that are to be sampled for "Container 1" with tabs 318 and 320 including similar listings for the additional containers. As is seen in the display section 306, each increment to be sampled is provided an identifier (e.g., a number is this embodiment) and corresponds to a shaded increment in the 3D model 308. In some embodiments, the shaded increments in the 3D model 308 will include an identifier that corresponds to that listed in the display section 306. Thus, in such an embodiment, the user, sampler, technician, etc., may easily visualize which increments have been sampled (FIG. 3B illustrates that the listing of increments 316 may provide a visual indicator that user input has been entered). In one embodiment, such an identifier may appear when user input "hovers" over a shaded increment (e.g., a mouse is placed over the shaded increment or touch-input is received for a predetermined amount of time). As shown in FIG. 3A, the text shown in the text boxes of the display section 306 corresponds to the recommended sampling amount for each increment. Further, an indicator adjacent to each text box states "SAVE" indicating that user input has not been received for any of the increments.

Referring now to FIG. 3B, an exemplary embodiment of the interactive user interface illustrating the rendered updated 3D model of the sampling plan from FIG. 3A is shown in accordance with some embodiments. The display section 306 of FIG. 3B illustrates that user input has been received for a plurality of increments (i.e., a plurality of increments have been sampled). Specifically, "Increment 3" has been sampled and the value 2.45 has been entered into the corresponding text box, wherein the value 2.45 corresponds to a standard of measurement (e.g., weight in grams or pounds). Similarly, "Increment 8" has been sampled and a value of 2.34 has been received by the display section 306. In one embodiment, the verification process discussed above with respect to the button 314 may be implemented as user input is received. For example, in response to receipt of user input indicating a sampling amount for a particular increment, the SPG system 610 may perform a verification process to ensure that the entered value is within a specified range, as discussed above.

Additionally, FIG. 3B illustrates that in some embodiments, when user input is received that varies from the recommended amount, the SPG system 610 may automatically recalculate the recommended sampling value for the increments to be sampled. For example, comparing "Increment 3" in FIGS. 3A-3B, the recommended sampling value was 2.19 while the actual sampling value (or amount) was 2.45. In such an example, the SPG system 610 has recalculated the recommended sampling value for "Increment 1" and "Increment 2" based on the actual sampling value for "Increment 3" (note that the actual sampling value "Increment 8" also varies from the recommended sampling value, which may also factor into the recalculation).

Figure 4:
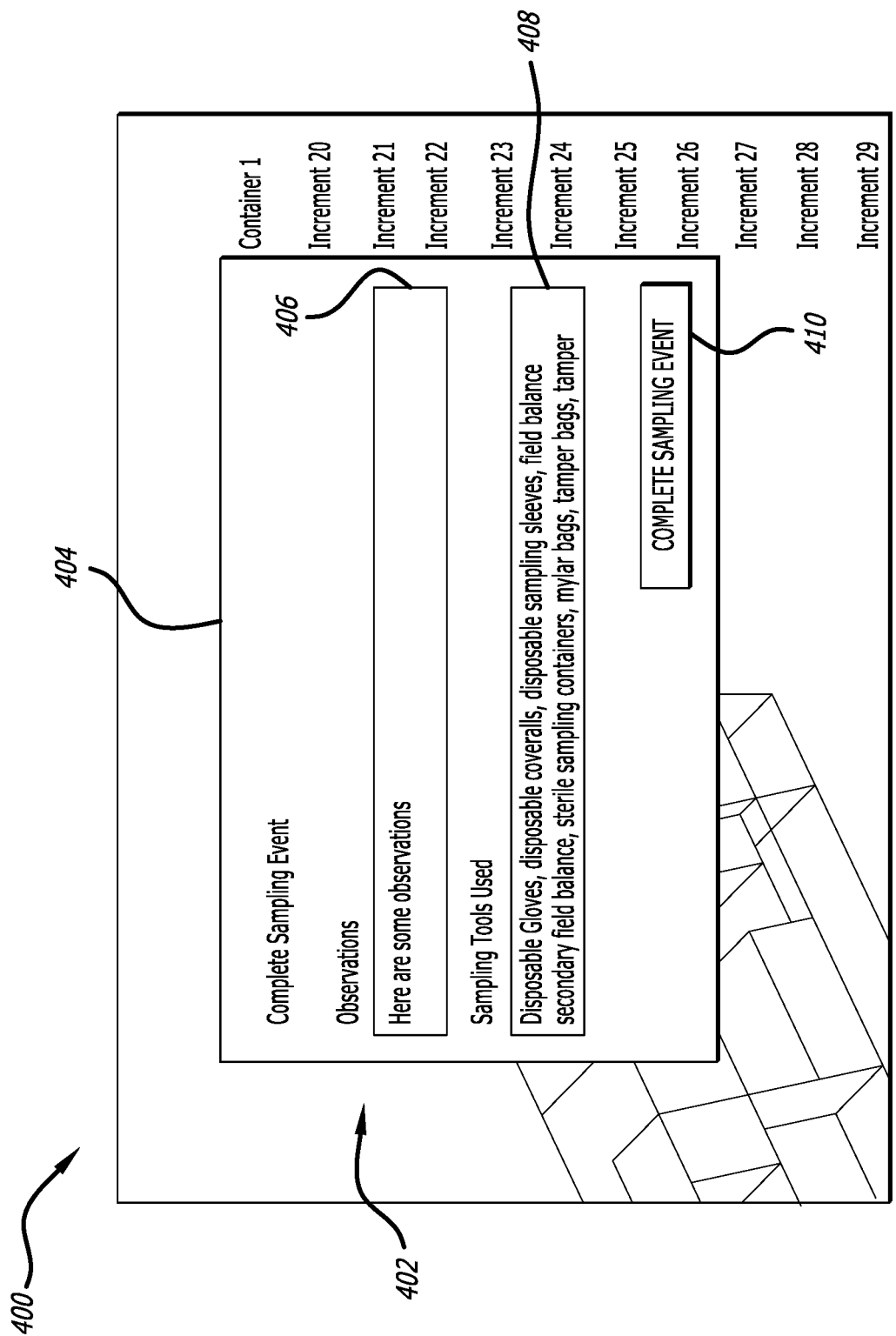
FIG. 4 is an exemplary embodiment of a ninth interactive user interface configured to receive user input corresponding to the completion of the 3D model of the sampling plan by the automated representative sampling plan generation system of FIG. 6 in accordance with some embodiments.

Referring now to FIG. 4, an exemplary embodiment of an interactive user interface configured to receive user input corresponding to the completion of the 3D model of the sampling plan by the automated representative sampling plan generation system of FIG. 6 is shown in accordance with some embodiments. The interactive UI 400 includes a display screen 402 behind a pop-up 404. The pop-up 404 is configured to receive user input corresponding to the completion of the sampling event (also referred to as a "sampling process" or a "sampling procedure"; these terms are used interchangeably throughout). Specifically, a button 410 is configured to receive user input (e.g., activation thereof), which initiates a completion process. In one embodiment, in response to activation of the button 410, the SPG system 610 may perform a verification process of the received input (corresponding to the actual sampled values) as discussed above as part of the completion process. Additionally, the pop-up 404 includes text fields 406 and 408 configured to receive user input pertaining to additional details of the sampling event such as technician observations and a listing of the sampling tools used. Other text boxes may be provided, wherein the information provided to the text boxes may be utilized in the automatic generation of a sampling report, discussed below.

Figure 5A:
FIG. 5A is an exemplary embodiment of a sampling event log automatically generated by the automated representative sampling plan generation system of FIG. 6 upon completion of a sampling process in accordance with some embodiments.

Referring to FIG. 5A, an exemplary embodiment of a sampling event log automatically generated by the automated representative sampling plan generation system of FIG. 6 upon completion of a sampling process is shown in accordance with some embodiments. FIG. 5A illustrates an exemplary sampling report 500 that may be displayed as an interactive user interface, transmitted via email, uploaded to a web portal (e.g., a cloud computing storage platform) for retrieval and/or mailed to one or more intended recipients. The sampling report 500 includes a header section 502 and a body section 504. The header section 502 is shown as including information pertaining to the company performing the sampling process (506) and information pertaining to the company having the sampling process performed (508).

The body section 504 includes customer and sample information 510, which may include one or more cultivators from which the substance being sampled was obtained (e.g., a cultivator when sampling plant products such as *cannabis*). In addition, the customer and sample information 510 may also include details of the substance being sampled (e.g., a sample name, a sample matrix, a batch identifier, etc.). Further, the body section 504 may include sampling information 512 pertaining to information of a sampling technician performing the sampling process and information detailing the sampling process (e.g., number of containers/packages sampled, sample weight, date/time of the sampling process, etc.). The sampling information 512 may also include additional text, such as that provided by the sampling technician in the pop-up 404 corresponding to the completion of the sampling event as seen in FIG. 4. The body section 504 may also include additional sampling details 514 including specific container information, a 3D model 516 of the corresponding container (e.g., Container 1) and an increment table 518 corresponding to specific details of the sampling with respect to the container.

Figure 5B:
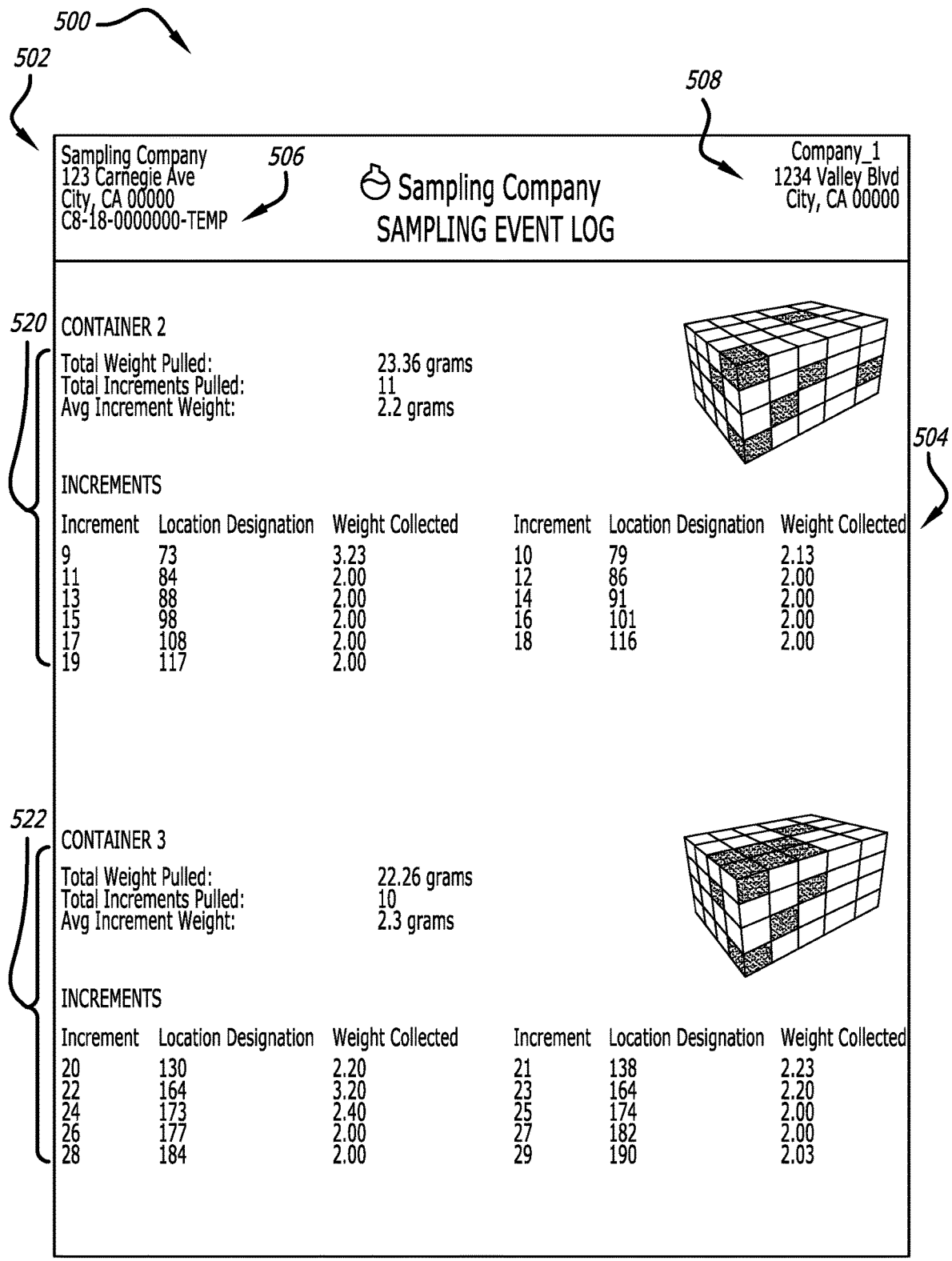
FIG. 5B is an exemplary embodiment of a second portion of the sampling event log of FIG. 5A automatically generated by the automated representative sampling plan generation system of FIG. 6 upon completion of a sampling process in accordance with some embodiments.

Referring to FIG. 5B, an exemplary embodiment of a second portion of the sampling event log of FIG. 5A automatically generated by the automated representative sampling plan generation system of FIG. 6 upon completion of a sampling process is shown in accordance with some embodiments. The sampling report 500 illustrated in FIG. 5B is an extension of the sampling report 500 as seen in FIG. 5A, e.g., a second page. The sampling report 500 as shown in FIG. 5B includes container specific information 520, which relates to "Container 2" and container specific information 522, which relates to "Container 3."

Referring to FIG. 6, an exemplary embodiment of a logical representation of the automated representative sampling plan generation system is shown in accordance with some embodiments. The SPG system 610 may be stored on persistent storage, such as the persistent storage 608 of a network device 600, which may be an electronic device such as a smart phone, a tablet, etc., that includes circuitry within the housing, namely one or more processors 602 that are coupled to a communication interface 604. The communication interface 604, in combination with communication interface logic 606, enables communications with external network devices, storage devices (e.g., the sampling plan data store 624) and/or networks such as the internet. According to one embodiment of the disclosure, the communication interface 604 may be implemented as a physical interface including one or more ports for wired connectors. Additionally, or in the alternative, the communication interface 604 may be implemented with one or more radio units for supporting wireless communications with other electronic devices. The communication interface logic 606 may include logic for performing operations of receiving and transmitting one or more communications including data via the communication interface 604 to enable communication between the SPG system 610 via a network (e.g., the internet or a LAN) and/or cloud computing services.

According to one embodiment of the disclosure, the SPG system 610 may include (a) sampling environment conditions input logic 612, (b) representative sampling plan design and generation logic 614, (c) 3D modeling generation and interactive display logic 616, (d) sample increments and recording logic 618, (e) real-time feedback logic 620, (f) automated report generation logic 622. Of course, when implemented as either software, firmware or hardware, one or more of these logic units could be implemented in combination or separately from each other.

The sampling environment conditions input logic 612 may be configured, upon execution by one or more processors, to determine the plurality of input fields to be displayed in an interactive UI so that the SPG system 610 may receive user input pertaining to sampling environment conditions as discussed above. Based on user input indicating whether the sampling is to be bulk sampling or package sampling, the sampling environment conditions input logic 612 selects particular input fields to be displayed. The SPG system 610 may receive updates, e.g., via configuration files, that may include alternative input fields over time. Additionally, the sampling environment conditions input logic 612 may be configured to automatically determine one or more sampling environment conditions (e.g., not displayed in an input field). Such automatic determinations may be based on laws, regulations, ordinances, contracts, etc. For example, automatic determinations may be made based on an analysis of configuration files or default configurations of the SPG system 610 such that one or more configuration files or default configurations may indicate that for particular user input received (e.g., the type of sampling, substance to be sampled, amount of substance to be sampled, location at which the substance was cultivated or obtained, etc.) based on laws, regulations, ordinances, contracts, etc. In one example, samplings performed of particular plant substances in California may be required by state and local laws or regulations. Therefore, the sampling environment conditions input logic 612 may analyze configuration files that indicate how sampling for such substances is to be performed in order to confirm or adhere to the requisite laws or regulations. Similarly, configuration files may be provided to the sampling environment conditions input logic 612 that indicate contractual rules for sampling particular substances provided by particular companies. Such configuration files may be received via a communication interface and stored in the sampling plan data store 624. In some embodiments, the SPG system 610 may be configured to access a blockchain. For instance, one or more contracts and/or configuration files may be stored on the blockchain.

The representative sampling plan design and generation logic 614 may be configured, upon execution by one or more processors, to automatically generate a representative sampling plan based on at least a portion of the user input received in the input fields as determined by the sampling environment conditions input logic 612 and, optionally, environment conditions determined by the sampling environment conditions input logic 612 according to laws, regulations, ordinances, contracts, etc. For instance, the representative sampling plan design and generation logic 614 may analyze one or more rule sets that set forth a methodology for generating a representative sampling plan. The one or more rule sets may be predetermined and/or dynamic configuration files that may be updated as discussed above. In addition, the rule sets may be generated and updated to ensure the generated sampling plan results in a sampling procedure that adheres to all applicable laws, regulations, ordinances, etc. Similarly, the one or more rule sets may be generated according to one or more contracts, such that when the SPG system 610 is generating a representative sampling plan for a particular company, a rule set based on one or more contracts may be referenced and analyzed during generation of the sampling plan.

The 3D modeling generation and interactive display logic 616 may be configured, upon execution by one or more processors, to generate the interactive displays and updates thereto as discussed above and illustrated in FIGS. 2A-4, for example. In particular, the 3D modeling generation and interactive display logic 616 may generate a data object of a 3D model of the representative sampling plan on a per container/package basis, such as the 3D model 308 seen in FIGS. 3A-3B. The 3D modeling generation and interactive display logic 616 may analyze the representative sampling plan and, according to one or more rule sets, generate a data object of a 3D model of a particular container/package. In addition, when the 3D model is to be regenerated based on user input as discussed above, the 3D modeling generation and interactive display logic 616 regenerates the data object of the 3D model according to the one or more rule sets as well as the user input.

The sample increments and recording logic 618 may be configured, upon execution by one or more processors, to receive user input via the listing of text boxes 316 as seen in FIGS. 3A-3B and record such data in, for example, the sampling plan data store 624. Such data may also be stored in cloud computing services, not shown.

The real-time feedback logic 620 may be configured, upon execution by one or more processors, to update the interactive UIs discussed above in combination with the 3D modeling generation and interactive display logic 616. The real-time feedback logic 620 may provide real-time feedback pertaining to user input (e.g., user input of incorrect format received, e.g., alphanumeric text when numeric text expected/required). For example, the real-time feedback logic 620 may cause a visual indicator (e.g., red highlighting, pop-up, etc.) to appear on the interactive UI providing feedback to the user that the user input received was incorrect.

Finally, the automated report generation logic 622 may be configured, upon execution by one or more processors, to automatically generate a sampling report, such as the sampling report 500 as seen in FIGS. 5A-5B. The automated report generation logic 622 may access the sampling plan data store 624 to retrieve data pertaining to the sampling event (e.g., company and technician information, the representative sampling plan, the 3D model(s), the user input, etc.). The retrieved data may be utilized to automatically generate a sampling report corresponding to the sampling event. In some embodiments, the report may have a standardized format. In other embodiments, one or more rule sets may indicate specific report formats based on, for example, the company having the sampling performed, the substance being sampled, a regulatory body or inspection authority that will receive a copy of the sampling report, etc.

In the foregoing description, the invention is described with reference to specific exemplary embodiments thereof. It will, however, be evident that various modifications and changes may be made thereto without departing from the broader spirit and scope of the invention as set forth in the appended claims.

What is claimed is:

1. A non-transitory storage medium having stored thereon logic, the logic being executable by one or more processors to perform operations including:
   determining, according to first user input received via a user interface (UI), a type of sampling to be performed; and
   generating (i) a randomized sampling plan for a substance stored in a first container, and (ii) a corresponding data object representing a three-dimensional (3D) model of the first container, wherein the 3D model includes a plurality of increments, wherein a subset of the plurality of increments to be sampled includes a visual indicator.

2. The non-transitory storage medium of claim 1, wherein a first type of sampling to be performed is bulk sampling, and a second type of sampling to be performed in packaged sampling.

3. The non-transitory storage medium of claim 2, wherein the logic being executable by the one or more processors to perform further operations including:
   receiving additional user input, via the UI, corresponding to information pertaining to sampling environment conditions.

4. The non-transitory storage medium of claim 1, wherein the sampling environment conditions for bulk sampling include at least one of a container size of the first container, an amount of the substance to be sampled, a minimum of percentage of the substance to be sampled, a total weight or total units of the substance to be sampled, minimum sample increment dimensions.

5. The non-transitory storage medium of claim 1, wherein the logic being executable by the one or more processors to perform further operations including:
   receiving additional user input corresponding to an actual sampled value for a first increment, the first increment included in the subset of the plurality of increments to be sampled.

6. The non-transitory storage medium of claim 5, wherein the logic being executable by the one or more processors to perform further operations including:
   performing a verification process to determine whether the actual sampled value for the first increment conforms to one or more law, rules regulation, or contract.

7. The non-transitory storage medium of claim 6, wherein the logic being executable by the one or more processors to perform further operations including:
   responsive determining the actual sampled value for the first increment does not conform to one or more law, rules regulation, or contract, causing an indicator to be provided indicating the actual sampled value for the first increment does not conform to one or more law, rules regulation, or contract.

8. The non-transitory storage medium of claim 1, wherein the logic being executable by the one or more processors to perform further operations including:
   causing the UI to be rendered to display a recommended sampling value for each increment of the subset of the plurality of increments to be sampled; and
   responsive to receiving additional user input corresponding to an actual sampled value for a first increment of the subset of the plurality of increments to be sampled, automatically recalculating the recommended sampling value for at least one increment of the subset of the plurality of increments to be sampled.

9. The non-transitory storage medium of claim 1, wherein the 3D model is configured to be rotatable on one or more axes according to additional user input.

10. A method comprising:
    determining, according to first user input received via a user interface (UI), a type of sampling to be performed; and
    generating (i) a randomized sampling plan for a substance stored in a first container, and (ii) a corresponding data object representing a three-dimensional (3D) model of the first container, wherein the 3D model includes a plurality of increments, wherein a subset of the plurality of increments to be sampled includes a visual indicator.

11. The method of claim 10, wherein a first type of sampling to be performed is bulk sampling, and a second type of sampling to be performed in packaged sampling.

12. The method of claim 11, wherein the logic being executable by the one or more processors to perform further operations including:
    receiving additional user input, via the UI, corresponding to information pertaining to sampling environment conditions.

13. The method of claim 10, wherein the sampling environment conditions for bulk sampling include at least one of a container size of the first container, an amount of the substance to be sampled, a minimum of percentage of the substance to be sampled, a total weight or total units of the substance to be sampled, minimum sample increment dimensions.

14. The method of claim 10, wherein the logic being executable by the one or more processors to perform further operations including:
    receiving additional user input corresponding to an actual sampled value for a first increment, the first increment included in the subset of the plurality of increments to be sampled.

15. The method of claim 14, wherein the logic being executable by the one or more processors to perform further operations including:
    performing a verification process to determine whether the actual sampled value for the first increment conforms to one or more law, rules regulation, or contract.

16. The method of claim 15, wherein the logic being executable by the one or more processors to perform further operations including:
    responsive determining the actual sampled value for the first increment does not conform to one or more law, rules regulation, or contract, causing an indicator to be provided indicating the actual sampled value for the first increment does not conform to one or more law, rules regulation, or contract.

17. The method of claim 10, wherein the logic being executable by the one or more processors to perform further operations including:
    causing the UI to be rendered to display a recommended sampling value for each increment of the subset of the plurality of increments to be sampled; and
    responsive to receiving additional user input corresponding to an actual sampled value for a first increment of the subset of the plurality of increments to be sampled, automatically recalculating the recommended sampling value for at least one increment of the subset of the plurality of increments to be sampled.

18. The method of claim 10, wherein the 3D model is configured to be rotatable on one or more axes according to additional user input.

19. A non-transitory storage medium having stored thereon logic, the logic comprising:
    a sampling environment conditions input logic module configured to, upon execution by one or more processors, determine a plurality of input fields to be displayed in an interactive user interface (UI) configured to receive user input pertaining to sampling environment conditions pertaining to a sampling procedure;
    a representative sampling plan design and generation logic module configured to, upon execution by the one or more processors, automatically generate a representative sampling plan based on at least a portion of the sampling environment conditions and one or more of a law, a regulation, an ordinance, or a contract,
        wherein the representative sampling plan includes (i) recommended sampling values, and (ii) a corresponding data object representing a three-dimensional (3D) model of a first container storing a substance to be sampled, the 3D model including a plurality of increments, wherein a subset of the plurality of increments to be sampled includes a visual indicator,
    a 3D modeling generation and interactive display logic module configured to, upon execution by the one or more processors, generate, according to at least the representative sampling plan; and
    a sample increments and recording logic module configured to, upon execution by the one or more processors, receive additional user input corresponding to an actual sampled value for a first increment, the first increment included in the subset of the plurality of increments to be sampled.

20. The non-transitory storage medium of claim 19, wherein the logic further comprises:
    an automated report generation logic module configured to, upon execution by the one or more processors, automatically generate a sampling report that includes results of the sampling procedure performed in accordance with the representative sampling plan.

\* \* \* \* \*